(12) United States Patent
Bleger et al.

(10) Patent No.: US 8,754,255 B2
(45) Date of Patent: Jun. 17, 2014

(54) PROCESS OF PREPARATION OF GLYOXYLIC ACID AQUEOUS SOLUTION

(75) Inventors: François Bleger, Geispolsheim Gare (FR); Olivier Simon, Jaux (FR); Alain Schouteeten, Ezanville (FR)

(73) Assignee: Clariant Specialty Fine Chemicals (France), Trosly Breuil (FR)

( * ) Notice: Subject to any disclaimer, the term of this patent is extended or adjusted under 35 U.S.C. 154(b) by 882 days.

(21) Appl. No.: 12/864,394

(22) PCT Filed: Jan. 21, 2009

(86) PCT No.: PCT/EP2009/050661
§ 371 (c)(1),
(2), (4) Date: Sep. 17, 2010

(87) PCT Pub. No.: WO2009/092734
PCT Pub. Date: Jul. 30, 2009

(65) Prior Publication Data
US 2011/0012056 A1    Jan. 20, 2011

(30) Foreign Application Priority Data
Jan. 25, 2008 (FR) ..................... 08 50473

(51) Int. Cl.
*C07C 51/235* (2006.01)
*C07C 51/27* (2006.01)

(52) U.S. Cl.
USPC ............... 562/531; 562/577; 252/182.12

(58) Field of Classification Search
CPC .............................. C07C 51/27; C07C 51/235
USPC ............... 252/182.12; 562/531, 577
See application file for complete search history.

(56) References Cited

U.S. PATENT DOCUMENTS

| | | | |
|---|---|---|---|
| 3,779,876 A | 12/1973 | Michelet | |
| 4,146,731 A * | 3/1979 | Ogahara et al. | 562/531 |
| 4,698,441 A | 10/1987 | Mitani et al. | |
| 5,091,566 A * | 2/1992 | Schouteeten et al. | 562/531 |
| 5,138,096 A * | 8/1992 | Schouteeten et al. | 562/531 |
| 2010/0312011 A1 | 12/2010 | Simon | |

FOREIGN PATENT DOCUMENTS

| | | |
|---|---|---|
| CN | 1634847 | 7/2005 |
| EP | 0349406 | 1/1990 |
| EP | 0428429 | 5/1991 |
| FR | 2372141 | 6/1978 |
| FR | 2516506 | 5/1983 |
| JP | 58153575 | 12/1983 |

OTHER PUBLICATIONS

Stitt ("Alternative multiphase reactors for fine chemcials A world beyond stirred tanks?" Chemical Engineering Journal, 90, (2002) 47-60).*
Garg Scientific (http://web.archive.org/web/20061016221728/http://gargscientific.com/gasliquid.htm) Oct. 16, 2006, accessed at http://web.archive.org on Aug. 8, 2013.*
English Translation of CN 1634874, Dec. 2, 2004.
International Search Report for PCT/EP2009/050661, dated Jul. 9, 2009.
Translation of Written Opinion of the Internatonal Searching Authority for PCT/EP2009/050661, dated Apr. 8, 2010.
International Search Report for PCT/EP2009/050663, dated Apr. 14, 2009.
Written Opinion of the International Searching Authority for PCT/EP2009/050663, dated Apr. 14, 2009.
English Abstract for JP 58 153575, Mar. 4, 1982.
Chemical Engineering and Processing, 33, (1994), 247-260.
Zhou Zhi-ming, et al., "A Novel Synthesis of Glyoxylic Acid with $O_2$ Catalysed by Nitrogen Oxide", Transactions of Beijing Institute of Technology, vol. 25, No. 5, May 2005.

* cited by examiner

*Primary Examiner* — Peter F Godenschwager
(74) *Attorney, Agent, or Firm* — Michael W. Ferrell

(57) ABSTRACT

The invention relates to a method for preparing an aqueous solution of glyoxylic acid by oxidation of an aqueous solution of glyoxal with oxygen or a gas containing oxygen, in the presence of a catalytic quantity of nitric acid and/or at least one nitrogen oxide, a strong acid not oxidizing glyoxal, and by maintaining conditions satisfying the equation $K_La/Q>10$, where $K_La$ is the total volumetric mass transfer coefficient and Q is the heat load liberated by the reaction per mole of glyoxal.

24 Claims, No Drawings

PROCESS OF PREPARATION OF GLYOXYLIC ACID AQUEOUS SOLUTION

The present invention relates to an industrial method for obtaining aqueous solutions of glyoxylic acid.

The use of oxygen to oxidize aqueous solutions of glyoxal to aqueous solutions of glyoxylic acid is known.

The method described in patent application FR-A-2372141 is carried out in the presence of 4 to 10% by weight of nitric acid in the reaction solution. Since the oxidation reaction is exothermic, a safety problem may arise with this quantity of acid in case of failure of the cooling system. Moreover, the method produces aqueous solutions of glyoxylic acid containing residual nitric acid which must be removed by laborious and/or costly subsequent treatments such as electrodialysis.

Patent applications EP-A-349406 and CN-A-1634847 teach the use of nitric oxide (NO) or sodium nitrite ($NaNO_2$) as oxidation catalysts, in the presence of a strong inorganic acid such as hydrochloric acid. However, these methods generate large quantities of $N_2O$ due to the nitric acid consumption, which are released into the atmosphere or must be treated by destructive methods.

The present invention eliminates the abovementioned drawbacks and serves:

to obtain a high glyoxylic acid yield,
to obtain a high glyoxal conversion,
to decrease the consumption of nitric acid and/or nitrogen oxides,
to decrease the formation of $N_2O$ gas which is harmful to the environment,
to minimize the formation of oxalic acid as by-product, and
to avoid a high residual nitric acid concentration in the final glyoxylic acid solution.

The invention therefore relates to a method for preparing an aqueous solution of glyoxylic acid by oxidation of an aqueous solution of glyoxal with oxygen or a gas containing oxygen, characterized in that the said oxidation is effected in the presence of a catalytic quantity of nitric acid and/or at least one nitrogen oxide, of between 0.005 and 0.1 mole per mole of glyoxal,
in the presence of a strong acid not oxidizing glyoxal, and
by maintaining conditions satisfying the equation $K_L a/Q > 10$, where $K_L a$ is the total volumetric mass transfer coefficient ($h^{-1}$) and Q is the heat load liberated by the reaction (watts/mole of glyoxal).

In the method according to the invention as described above and in the rest of the description, the quantity of glyoxal, expressed in moles, is the quantity of glyoxal used in the aqueous solution at the start of the oxidation reaction.

In the invention, the oxidation catalyst may be selected from nitric acid and/or a nitrogen oxide. Between about 0.005 and 0.1 mole of catalyst is generally used, preferably between about 0.01 and 0.07 mole of catalyst, and particularly between about 0.01 and 0.06 mole of catalyst, per mole of glyoxal.

The nitrogen oxides may be selected from the following gases: nitric oxide (NO), nitrogen dioxide ($NO_2$), nitrogen tetroxide ($N_2O_4$), nitrogen trioxide ($N_2O_3$) or mixtures thereof.

As nitrogen oxides, mention can be made of metal salts of nitric acid or nitrous acid such as sodium nitrite, potassium nitrite, sodium nitrate, potassium nitrate, silver nitrate, copper nitrate or mixtures thereof.

According to a preferred aspect of the implementation of the invention, nitric acid is used as an oxidation catalyst. The grade and concentration of the nitric acid may be similar to those used in conventional methods of oxidation by nitric acid. As an example, mention can be made of aqueous solutions of nitric acid in a concentration of 20 to 68% by weight.

The inventive method is implemented in the presence of a strong acid which does not oxidize the glyoxal. It is preferable to use a quantity of between 0.05 and 1 mole of strong acid per mole of glyoxal, and particularly a quantity of between 0.2 and 0.7 mole of strong acid per mole of glyoxal.

In the context of the present invention, "strong acid" means an acid having a pKa lower than 1. Among the strong acids not oxidizing glyoxal, mention can be made, as examples, of hydrochloric acid, hydrobromic acid, sulphuric acid, sulphonic acids such as p-toluenesulphonic acid, methane sulphonic acid or mixtures thereof, or more particularly hydrochloric acid.

As other examples of strong acids not oxidizing glyoxal, mention can be made of ion exchange resins of the sulphonic type which are sold under various trade names, such as Amberlyst® 15 and Dowex® 50WX resins. The abovementioned resins consist of a polystyrene skeleton which carries sulphonic groups.

Other types of commercial resins may be suitable such as perfluorinated resins bearing sulphonic groups such as Nafion® resins.

Advantageously, strong acids are used in aqueous solution and, preferably, hydrochloric acid in aqueous solution in a concentration of 10 to 37% by weight.

According to an alternative of the inventive method, a compound generating a strong acid not oxidizing glyoxal can be used.

In the context of the present invention, "compound generating a strong acid not oxidizing glyoxal" means any compound capable of reacting with water to generate a strong acid such as defined previously. By way of example, mention can be made of thionyl chloride ($SOCl_2$), and Lewis acids such as $AlCl_3$.

Increasing the transfer between the gases and the liquid of the reaction system is an important feature of the present invention, because it serves to decrease the input of nitric acid and/or nitrogen oxide while preserving, on the one hand, a good glyoxylic acid yield and, on the other, a high glyoxal conversion rate.

According to the invention, the ratio of the total volumetric mass transfer coefficient $K_L a$ ($h^{-1}$) to the heat load liberated by the reaction Q (watts/mole of glyoxal), must be such that $K_L a/Q$ is higher than 10.

The value of the total volumetric mass transfer coefficient can be determined by the method of oxidation of sodium sulphite by air as described in the article in Chemical Engineering and Processing, 33, (1994), 247-260.

For the equation $K_L a/Q > 10$ to be satisfied, it is important, on the one hand, to adjust the total volumetric mass transfer coefficient and, on the other, the temperature of the liquid phase of the reaction medium and the inlet flow rate of oxygen or of the gas containing oxygen.

The first condition is generally satisfied by selecting a reaction apparatus designed to obtain a high exchange surface area between the gas phase and the liquid phase and thereby obtaining a high value of $K_L a$.

Preferably, the reaction is carried out under conditions such that the coefficient $K_L a$ is between 100 $h^{-1}$ and 1000 $h^{-1}$.

To implement the inventive method, use can be made, for example, of an apparatus comprising reactors with a suction jet mixing nozzle placed internally or externally.

According to a preferred embodiment, a closed circuit reactor is used with a built-in suction jet mixing nozzle, an external liquid phase flow duct connected to the ejector and comprising a pump.

Use can also be made, for example, of an apparatus comprising stirred gas liquid reactors or bubble columns comprising packings.

The value of $K_La$ is adjusted by means of appropriate technical measures, adapted to each type of reactor. The inventive method is advantageously implemented in a reactor with a suction jet mixing nozzle (jet reactor).

The heat load Q liberated by the oxidation reaction can be determined from the following equation:

$$Q = D \times Cp_{water} \times \Delta t / nG$$

where:

D is the flow rate of water for cooling the reactor,
Cp is the heat capacity of the water and,
$\Delta t$ is the difference between the cooling water inlet temperature and outlet temperature,
nG is the number of moles of glyoxal.

Preferably, the reaction is carried out under conditions such that the value of Q is between 5 and 150 watts/mole of glyoxal. The value of Q can be adjusted by a variation in various parameters such as the liquid phase temperature which affects the oxidation rate, and, in consequence, the heat liberated by the oxidation reaction, or the inlet flow rate of the oxygen or of a gas containing oxygen.

According to another alternative of the invention, the ratio of the total volumetric mass transfer coefficient $K_La$ ($h^{-1}$) to the heat load liberated by the reaction Q (watts/mole of glyoxal), must be such that $10 < K_La/Q \leq 100$.

The inventive method is generally implemented by adding an aqueous solution of hydrochloric acid to an aqueous solution of glyoxal, while introducing an aqueous solution of nitric acid and optionally by adding sodium nitrite to the reaction medium, and finally by introducing oxygen or a gas containing oxygen, such as air, under a pressure of between 200 and about 3000 kPa.

Preferably, oxygen is used. In this case, the oxygen consumption is between 0.5 and about 1 mole per mole of glyoxal.

As aqueous solutions of glyoxal, use can be made of aqueous solutions of glyoxal available in the industry, normally containing 5 to 50% by weight of glyoxal.

The reaction normally takes place at a temperature between ambient temperature and about 85° C., advantageously between 35 and about 75° C. If necessary, the temperature can be adjusted in order to keep the heat load Q constant.

The reaction is generally continued for 1 to 20 hours.

The reaction mixture obtained can be used as such as an aqueous solution of glyoxylic acid in various applications. Alternatively, the oxalic acid can be separated from the reaction mixture by crystallization, to obtain an aqueous solution of glyoxylic acid. Advantageously, the reaction mixture can be further purified by means known per se such as distillation, treatment by ion exchange resin or electrodialysis.

The invention is illustrated in a non-limiting manner by the following examples.

EXAMPLE 1 a) Determination of the Total Mass Transfer Coefficient ($K_La$) of the Reactor

In a 20 L enameled steel gas liquid reactor, previously purged with nitrogen, equipped with a double jacket, an external loop for the liquid phase, comprising a pump and an ejector and an external loop for the gas phase connected to the ejector, 10 L of an aqueous solution is introduced containing 0.8 mol/L of sodium sulphite ($Na_2SO_3$) and containing $1.10^{-6}$ mol/L of cobalt sulphate ($CoSO_4$). The external circulation is started up at 500 L/h and the reactor is pressurized to 200 kPa (2 bar) of oxygen. The pressure is maintained constant at 200 kPa by adjusting the oxygen flow rate. The sodium sulphite consumption is measured to calculate the total mass transfer coefficient of the reactor.

The total mass transfer coefficient of the reactor measured by this method is 932 $h^{-1}$.

b) Preparation of the Aqueous Solution of Glyoxylic Acid

Into the same reactor is introduced 7250 g of an aqueous solution containing 40% by weight of glyoxal, 3400 g of an aqueous solution of hydrochloric acid containing 37% by weight and 2611 g of water. The mixture is heated to 45° C. by the double jacket. 140 g of nitric acid containing 68% by weight in water is then added. 10 minutes later, 6 g of $NaNO_2$ in solution in 150 g of water is introduced and the reactor is pressurized to 400 kPa (4 bar) with oxygen. The temperature is maintained constant at 43+/−5° C. so that the cooling load exchanged in the double jacket is 1500 W (Q=30 watts/mole of glyoxal) and the pressure is maintained constant at above 400 kPa by adding oxygen as required. After an addition of 400 NL (NormoLiter) of oxygen in about 2 h, the reaction medium is heated so as to reach 60° C. in about 1 h. The oxygen addition is stopped when reaching 628 NL.

When the reaction is complete (about 4 h after the introduction of $NaNO_2$), 14.24 kg of reaction mixture is obtained.

The reaction mixture contains 20.3% of glyoxylic acid, representing a yield of 78% and 0.5% of glyoxal representing a conversion of 97.5%.

The quantity of nitric acid consumed is less than 0.01 mole per mole of glyoxal (analyses of the gas phase at the end of the reaction by gas chromatography).

COMPARATIVE EXAMPLE 1

The procedure described in example 1 is repeated, except that the reaction is carried out under conditions such that $K_La/Q$ is lower than 10.

a) Determination of the Total Mass Transfer Coefficient ($K_La$) of the Reactor

In a 20 L enameled steel gas liquid reactor, previously purged with nitrogen, equipped with a double jacket, an external loop for the liquid phase, comprising a pump and an ejector and an external loop for the gas phase connected to the ejector, 10 L of an aqueous solution is introduced containing 0.8 mol/L of sodium sulphite ($Na_2SO_3$) and containing $1.10^{-6}$ mol/L of cobalt sulphate ($CoSO_4$). The external circulation is started up at 200 L/h and the reactor is pressurized to 2 bar of oxygen. The pressure is maintained constant at 200 kPa (2 bar) by adjusting the oxygen flow rate. The sodium sulphite consumption is measured to calculate the total mass transfer coefficient of the reactor.

The total mass transfer coefficient of the reactor measured by this method is 196 $h^{-1}$.

b) Preparation of the Aqueous Solution of Glyoxylic Acid

Into the same reactor is introduced 7250 g of an aqueous solution containing 40% by weight of glyoxal, 3400 g of an aqueous solution of hydrochloric acid containing 37% by weight and 2611 g of water. The mixture is heated to 45° C. by the double jacket. 140 g of nitric acid containing 68% by weight in water is then added. 10 minutes later, 6 g of NaNO$_2$ in solution in 150 g of water is introduced and the reactor is fed with oxygen at a rate of about 200 NL/h such that the heat load exchanged is 1500 W (Q=30 watts/mole of glyoxal). At the same time, 232 g of an aqueous solution of nitric acid containing 68% by weight is added at a rate of 2 g/min (if not, the reaction stops). The temperature is maintained constant at 43+/−2° C. After an addition of 400 NL of oxygen in about 2 h, a temperature ramp is applied in order to reach 60° C. in 1 h. The oxygen addition is stopped when reaching 601 NL. During the reaction, the pressure rises progressively to reach about 800 kPa (8 bar) gauge.

When the reaction is complete, 14.37 kg of reaction mixture is obtained.

The reaction mixture contains 18.8% of glyoxylic acid, representing a yield of 73% and 0.47% of glyoxal representing a conversion of 97.6%.

The results show that when the ratio $K_La/Q$ is lower than 10, in order to obtain a good glyoxylic acid yield and a good conversion, it is necessary to use a much larger quantity of nitric acid. In fact, the nitric acid is consumed during the reaction, causing the formation of undesirable by-products for the environment and a high concentration of residual nitric acid in the final glyoxylic acid solution.

EXAMPLE 2

The reactor described in example 1 is used with a $K_La$ of 932 h$^{-1}$ and a flow rate of 500 L/h in the external loop. Into this reactor is introduced 7250 g of an aqueous solution containing 40% by weight of glyoxal, 3400 g of an aqueous solution of hydrochloric acid containing 37% by weight and 2610 g of water.

The mixture is heated to 47° C. by the double jacket. 140 g of nitric acid containing 68% by weight in water is then added. 10 minutes later, 6 g of NaNO$_2$ in solution in 150 g of water is introduced and the reactor is pressurized to 400 kPa (4 bar) with oxygen. The temperature is maintained constant at 48+/−1° C. so that the cooling load exchanged in the double jacket is 2250 W (Q=45 watts/mole of glyoxal). The pressure is maintained constant at above 400 kPa by adding 322 NL/h (NormoLiter per hour) of oxygen as required. After an addition of 215 NL (NormoLiter) of oxygen in about 36 min, the reaction medium is heated so as to reach 55° C. in about 1 h in order to keep the heat load exchanged in the double jacket constant. When the quantity of oxygen added reaches 525 NL (NormoLiter), the temperature is increased in order to reach 65° C. in about 20 min. The oxygen addition is stopped when reaching 628 NL.

When the reaction is complete (about 2 h from the introduction of NaNO$_2$), 14.26 kg of reaction mixture is obtained.

The reaction mixture contains 19.9% of glyoxylic acid, representing a yield of 77% and less than 0.5% of glyoxal representing a conversion of 97.5%.

The quantity of nitric acid consumed is less than 0.01 mole per mole of glyoxal (analyses of the gas phase at the end of the reaction by gas chromatography).

EXAMPLE 3

The reactor described in example 1 is used with a $K_La$ of 932 h$^{-1}$ and a flow rate of 500 L/h in the external loop. Into the same reactor is introduced 7250 g of an aqueous solution containing 40% by weight of glyoxal, 3400 g of an aqueous solution of hydrochloric acid containing 37% by weight and 2610 g of water. The mixture is heated to 33° C. by the double jacket. 140 g of nitric acid containing 68% by weight in water is then added. 10 minutes later, 6 g of NaNO$_2$ in solution in 150 g of water is introduced and the reactor is pressurized to 400 kPa (4 bar) with oxygen. The temperature is maintained constant at 34+/−1° C. so that the cooling load exchanged in the double jacket is 95 W (Q=1.86 watts/mole of glyoxal). The pressure is maintained constant at above 400 kPa by adding 13 NL/h (NormoLiter per hour) of oxygen as required. After an addition of 250 NL (NormoLiter) of oxygen in about 18 h, the reaction medium is heated so as to reach 39° C. in about 18 h in order to keep constant the heat load exchange in the double jacket. When the quantity of oxygen added reaches 500 NL (NormoLiter), the temperature is increased in order to reach 48° C. in about 10 min. The oxygen addition is stopped when reaching 628 NL.

When the reaction is complete (about 46 h from the introduction of NaNO$_2$), 14.25 kg of reaction mixture is obtained.

The reaction mixture contains 20.3% of glyoxylic acid, representing a yield of 78% and less than 0.5% of glyoxal representing a conversion of 97.5%.

The quantity of nitric acid consumed is less than 0.01 mole per mole of glyoxal (analyses of the gas phase at the end of the reaction by gas chromatography).

EXAMPLE 4 a) Determination of the Total Mass Transfer Coefficient ($K_La$) of the Reactor

In a 20 L enameled steel gas liquid reactor, previously purged with nitrogen, equipped with a double jacket, an external loop for the liquid phase, comprising a pump and an ejector and an external loop for the gas phase connected to the ejector, 10 L of an aqueous solution is introduced containing 0.8 mol/L of sodium sulphite (Na$_2$SO$_3$) and containing $1.10^{-6}$ mol/L of cobalt sulphate (CoSO$_4$). The external circulation is started up at 400 L/h and the reactor is pressurized to 200 kPa (2 bar) of oxygen. The pressure is maintained constant at 200 kPa by adjusting the oxygen flow rate. The sodium sulphite consumption is measured to calculate the total mass transfer coefficient of the reactor.

The total mass transfer coefficient of the reactor measured by this method is 563 h$^{-1}$.

b) Preparation of the Aqueous Solution of Glyoxylic Acid

Into the same reactor is introduced 7250 g of an aqueous solution containing 40% by weight of glyoxal, 3400 g of an aqueous solution of hydrochloric acid containing 37% by weight and 2610 g of water. The mixture is heated to 38° C. by the double jacket. 140 g of nitric acid containing 68% by weight in water is then added. 10 min later, 6 g of NaNO$_2$ in solution in 150 g of water is introduced and the reactor is pressurized to 400 kPa (4 bar) with oxygen. The temperature is maintained constant at 38+/−1° C. so that the cooling load exchanged in the double jacket is 280 W (Q=5.6 watts/mole of glyoxal) and the pressure is maintained constant at above 400 kPa by adding oxygen as required. After an addition of 400 NL (NormoLiter) of oxygen in about 3 h, the reaction medium is heated so as to reach 44° C. in about 9 h in order to keep the heat load exchange in the double jacket constant. When the quantity of oxygen added reaches 500 NL (Normo- Liter), the temperature is increased in order to reach 53° C. in about 3 h. The oxygen addition is stopped when reaching 628 NL.

When the reaction is complete (about 15 h from the introduction of $NaNO_2$), 14.26 kg of reaction mixture is obtained.

The reaction mixture contains 20.2% of glyoxylic acid, representing a yield of 78% and 0.5% of glyoxal representing a conversion of 97.5%.

The quantity of nitric acid consumed is less than 0.01 mole per mole of glyoxal (analyses of the gas phase at the end of the reaction by gas chromatography).

The invention claimed is:

1. A process for preparing an aqueous solution of glyoxylic acid by oxidation of an aqueous solution of glyoxal with oxygen or a gas containing oxygen, wherein the oxidation is carried out
    in the presence of a catalytic quantity of nitric acid and/or at least one nitrogen oxide, of between 0.005 and 0.1 mole per mole of glyoxal,
    in the presence of a strong acid not oxidizing glyoxal, selected from the group consisting of hydrochloric acid, hydrobromic acid, sulfuric acid, sulfonic acids, ion exchange resins of the sulfonic type, perfluorinated resins bearing sulfonic groups or mixtures thereof, and
    by maintaining conditions satisfying the equation $K_La/Q>10$, where $K_La$ is the total volumetric mass transfer coefficient ($h^{-1}$) and Q is the heat load liberated by the reaction (watts/mole of glyoxal).

2. The process according to claim 1, wherein the catalytic quantity of nitric acid and/or nitrogen oxide is between 0.01 and 0.07 mole per mole of glyoxal.

3. The process according to claim 1, wherein the catalytic quantity of nitric acid and/or nitrogen oxide is between 0.005 and 0.06 mole per mole of glyoxal.

4. The process according to claim 1, wherein the nitrogen oxide is selected from the group consisting of the following gases: nitric oxide (NO), nitrogen dioxide ($NO_2$), nitrogen tetroxide ($N_2O_4$), nitrogen trioxide ($N_2O_3$) and mixtures thereof.

5. The process according to claim 1, wherein the nitrogen oxide is selected from the group consisting of metal salts of nitric acid, metal salts of nitrous acid and mixtures thereof.

6. The process according to claim 1, wherein the quantity of strong acid not oxidizing glyoxal is between 0.05 and 1 mole per mole of glyoxal.

7. The process according to claim 1, wherein the quantity of strong acid not oxidizing glyoxal is between 0.2 and 0.7 mole per mole of glyoxal.

8. The process according to claim 1, wherein the strong acid not oxidizing glyoxal is selected from the group consisting of hydrochloric acid, hydrobromic acid, sulphuric acid, p-toluenesulphonic acid and mixtures thereof.

9. The process according to claim 8, wherein the strong acid not oxidizing glyoxal is hydrochloric acid.

10. The process according to claim 1, wherein a compound generating a strong acid not oxidizing glyoxal, is used.

11. The process according to claim 1, wherein $K_La$ is between 100 $h^{-1}$ and 1000 $h^{-1}$.

12. The process according to claim 1, wherein the oxidation is carried out in an apparatus comprising a reactor with a suction jet mixing nozzle placed internally or externally.

13. The process according to claim 1, wherein the oxidation is carried out in an apparatus comprising a reactor in a closed circuit with a built-in suction jet mixing nozzle, an external liquid phase flow duct connected to the ejector and a pump.

14. The process according to claim 1, wherein the oxidation is carried out in an apparatus comprising stirred gas liquid reactors or bubble columns comprising packings.

15. The process according to claim 1, wherein Q is between 5 and 150 watts/mole of glyoxal.

16. The process according to claim 1, wherein the ratio of the total volumetric mass transfer coefficient $K_La$ ($h^{-1}$) to the heat load liberated by the reaction Q (watts/mole of glyoxal) is such that $10<K_La/Q\leq100$.

17. The process according to claim 1, wherein the oxygen or a gas containing oxygen is introduced under a pressure of between 200 and 3000 kPa.

18. The process according to claim 1, wherein oxygen is used.

19. The process according to claim 18, wherein the oxygen consumption is between 0.5 and 1 mole per mole of glyoxal.

20. The process according to claim 1, that it is carried out at a temperature between ambient temperature and 85° C.

21. The process according to claim 20, that it is carried out at a temperature between 35° C. and 75° C.

22. The process according to claim 1, wherein the reaction is carried out for 1 hour to 20 hours.

23. The process according to claim 1, wherein the reaction is carried out in the presence of nitric acid and a metal salt selected from sodium nitrite, potassium nitrite, sodium nitrate, potassium nitrate, silver nitrate, copper nitrate or mixtures thereof.

24. The process according to claim 1, wherein the reaction is carried out in the presence of nitric acid and the amount of nitric acid consumed is less than 0.01 mole per mole of glyoxal.

* * * * *